United States Patent [19]
Holbrook et al.

[11] Patent Number: 6,033,882
[45] Date of Patent: Mar. 7, 2000

[54] CHIRAL SYNTHESIS OF 2-HYDROXY CARBOXYLIC ACIDS WITH A DEHYDROGENASE

[75] Inventors: Joseph John Holbrook, Bath; Christine Louise Willis, Bristol; Keyji Johnsen, Bristol; Martin John Hateley, Bristol, all of United Kingdom

[73] Assignee: Genzyme Corporation, Cambridge, Mass.

[21] Appl. No.: 08/765,963

[22] PCT Filed: Jul. 7, 1995

[86] PCT No.: PCT/EP95/02692

§ 371 Date: May 29, 1997

§ 102(e) Date: May 29, 1997

[87] PCT Pub. No.: WO96/01892

PCT Pub. Date: Jan. 25, 1996

[30] Foreign Application Priority Data

Jul. 7, 1994 [GB] United Kingdom .................. 9413710

[51] Int. Cl.$^7$ .................................................. C12D 7/62
[52] U.S. Cl. ........................................ 435/135; 435/190
[58] Field of Search ................................. 435/190, 135

[56] References Cited

U.S. PATENT DOCUMENTS 5,098,841  3/1992  Ghisalba et al. ........................ 435/28

FOREIGN PATENT DOCUMENTS 0 130 288  4/1984  European Pat. Off. .
WO93/13215  7/1993  WIPO .

OTHER PUBLICATIONS

Nessler, S., et al. (1994) J. Mol. Biol. 235, 370–371.
Bernard, N. et al., "NAD Dependent D–2–Dhydroxyisocaptroate Dehydrogenase *Lactobacillus Delbrueckii* Subsp. *Bulgaricus* : Gene Cloning and Enzyme Characterization", *Eur. J. Biochem.*, 224. 439–446 (1994).
Bernard N. et al., "Cloning of the D–lactate Dehydrogenase Gene from *Lactobacillus Delbrueckii* Supsp. *Bulgaricus* by Complementation in *Escherichia Coli*", Federation of European Biochemical Societies, 290:1,2, 61–64 (1991).
Bernard, N. et al., "D175 Discriminates between NADH and NADPH in the Coenzyme Binding Site of *Lactobacilus Delbrueckii* Subsp. *Bulgaricus* D–Lactate Dehydrogenase" Biochemical and Biophysical Research Communications, 208:3, 895–900 (1995).
Bormann, C. et al., "Isolation of Streptomyces Tendae Mutants with an Altered Nikkomycin Spectrum", *Microbial. Biochem.*, III, 421 (1989), abstract 111:74493V.
Brown, R.B. et al., "Asymmetric Reduction of α–Keto Esters with Potassium", *J. Org. Chem.*, 51, 3396–3398 (1986).
Shaked, Z. et al., "Enzyme Catalyzed Organic Synthesis: HADH Regeneration by Using Formate Dehydrogenase", *J. Am. Chem. Soc.*, 102, 7104–7105 (1980).

Corey, E. J. et al., "A New System for Catalytic Enantioselective Reduction of a Chiral Ketones to Chiral Alcohols, Synthesis of Chiral α–Hydroxy Acids", *Tetrahedron Letters*, 31:5, 611–614 (1990).
Dale, J.A. et al., "α–Methoxy–α– Trifluoromethylphenylacetic Acid, a Versatile Reagent for the Determination of Enantiomeric Composition of Alcohols and Amines", *J. of Org. Chem.*, 34:9, 2543–2549 (1969).
Evans, D.A. et al., "Asymmetric Oxygenation of Chiral Imide Enolates. A General Approach to the Synthesis of Enantiomerically Pure α–Hydroxy Carboxylic Acid Synthons", *J. Am. Chem Soc.*, 107, 4346–4348 (1985).
Kalaritis, P. et al., "Kinetic Resolution of 2–Substituted Esters Catalyzed by a Lipase Ex. *Pseudomonas fluorescens*", *J. Org. Chem*, 55, 812–815 (1990).
Kim, M. et al., "Synthesis of Optically Pure (R)–2–Hydroxy Acids Using D–Lactate Dehydrogenase", *J. Chem. Soc., Chem. Commun.*, 326–327 (1991).
Kochhar, S. et al., "Primary Structure, Physicochemical Properties, and Chemical Modification of NAD+ –dependent +sc D–Lactate Dehydrogenase", *J. of Bio. Chem.*, 267:12, 8499–8513 (1992).
Kocchar, S. et al., "Cloning and Overexpression of the *Lactobacillus Bulgaricus* NAD+ –Dependent D–Lactate Dehydrogenase Gene in *Escherichia Coli:* Purification and Characterization of the Recombinant Enzyme", *Biochemical and Biophysical Research Communications*, 185:2, 705–712 (1992).
Nessler, S. et al., "Crystallization of D–Lactate Dehydrogenase from *Lactobacillus Bulgaricus*", Chemical Abstracts, 120, 450 (1994), abstract 120:1860501.
Philip, C.M. et al., "Preparation of Enantiometrically Enriched α–Hydroxy Acid Derivatives from α–Alkoxyorganostannanes", Tetrahedron Lett. 31:14, 1985–1988 (1990).
Simon, E.S. et al., "D–Lactate Dehydrogenase Substrate Specificity and Use as a Catalyst in the Synthesis of Homochiral 2–Hydroxy Acids", *Applied Biochemistry and Biotechnology*, 22, 169–179 (1989).
Ziegler, T. et al., "Ein Einfacher Zugang zu (R)–α–Hydroxycarbonsä uren and (R)–1–Amino–2–Alkoholen aus (R)–Cyanhydrinen", Synthesis, 575–578 (1990).

*Primary Examiner*—Charles L. Patterson, Jr.
*Attorney, Agent, or Firm*—Jennifer Tegfeldt

[57] ABSTRACT

Inter alia, an enzyme, a 2-hydroxy carboxylic acid dehydrogenase, characterised in that it is obtainable from *Lactobacillus delbrueckii* ssp. Bulgaricus and in that it catalyses the production of (R)-hydroxy derivatives of 2-keto acids, which are unsubstituted in the 3-position, but which may be substituted in the 4-position or beyond is disclosed.

2 Claims, 2 Drawing Sheets

CHIRAL SYNTHESIS OF 2-HYDROXY CARBOXYLIC ACIDS WITH A DEHYDROGENASE

This invention relates to chiral synthesis; more particularly, it relates to a broad specificity 2-hydroxy carboxylic acid dehydrogenase initially obtained from *Lactobacillus delbrueckii* ssp. Bulgaricus, but subsequently cloned, to sequence variants thereof and to the use of such enzymes as catalysts capable of preparation of the (R)-isomer at the 2-hydroxy group.

As will be appreciated, there are several aspects to the present invention. Firstly, the present enzyme was isolated from the above source by conventional means, but it is conveniently over-produced by cloning in an *E. coli* system, for example. Secondly, although the present enzyme, however obtained, is useful in the production of (R)-2-hydroxy acids, sequence variants thereof modified to supress inhibition of the enzyme activity by substrate offer further advantages. Such may be obtained by site directed mutagenesis. Thirdly, the present enzyme and sequence variants thereof may be used to catalyse the production of (R)-hydroxy derivatives of 2-keto acids, and hence esters, for example, which are unsubstituted in the 3-position, but may be substituted in the 4-position or beyond by a wide range of substituents including aliphatics, aromatics, heterocyclics and nitrogen-containing moieties.

In one embodiment, the present invention provides an enzyme, a 2-hydroxy carboxylic acid dehydrogenase, characterised in that it is obtainable from *Lactobacillus delbrueckii* ssp. Bulgaricus and in that it catalyses the production of (R)-hydroxy derivatives of 2-keto acids, which are unsubstituted in the 3-position, but which may be substituted in the 4-position or beyond.

In another embodiment, the present invention provides a process for the production of such an enzyme characterised in that it comprises isolation from *Lactobacillus delbrueckii* ssp. Bulgaricus or cloning.

In a further embodiment, the present invention provides a sequence variant of such an enzyme, which may be produced by such a process, characterised in that it has been modified so as to supress inhibition of the enzyme activity by substrate. For example, in one preferred illustration, Histidine 206 may be replaced by glutamine.

In yet another embodiment, the present invention provides a process for the production of such a variant characterised in that it comprises site directed mutagenesis.

In still another embodiment, the present invention provides a process for the production of a (R)-hydroxy derivative of a 2-keto acid characterised in that it comprises contacting the acid with such an enzyme or a sequence variant thereof, which may be produced by such processes. Preferably, the conditions, such as pH, are modified so as to provide maximal rate.

By way of illustration, the present invention, or even LDH obtained from *Staphylococcus epidermidis* and other sources, may be applied to the preparation of 3-cyclopentyl-2(R)-hydroxypropanoic acid.

Having indicated the nature and scope of the present invention, it will now be described in more detail.

Figure 1:
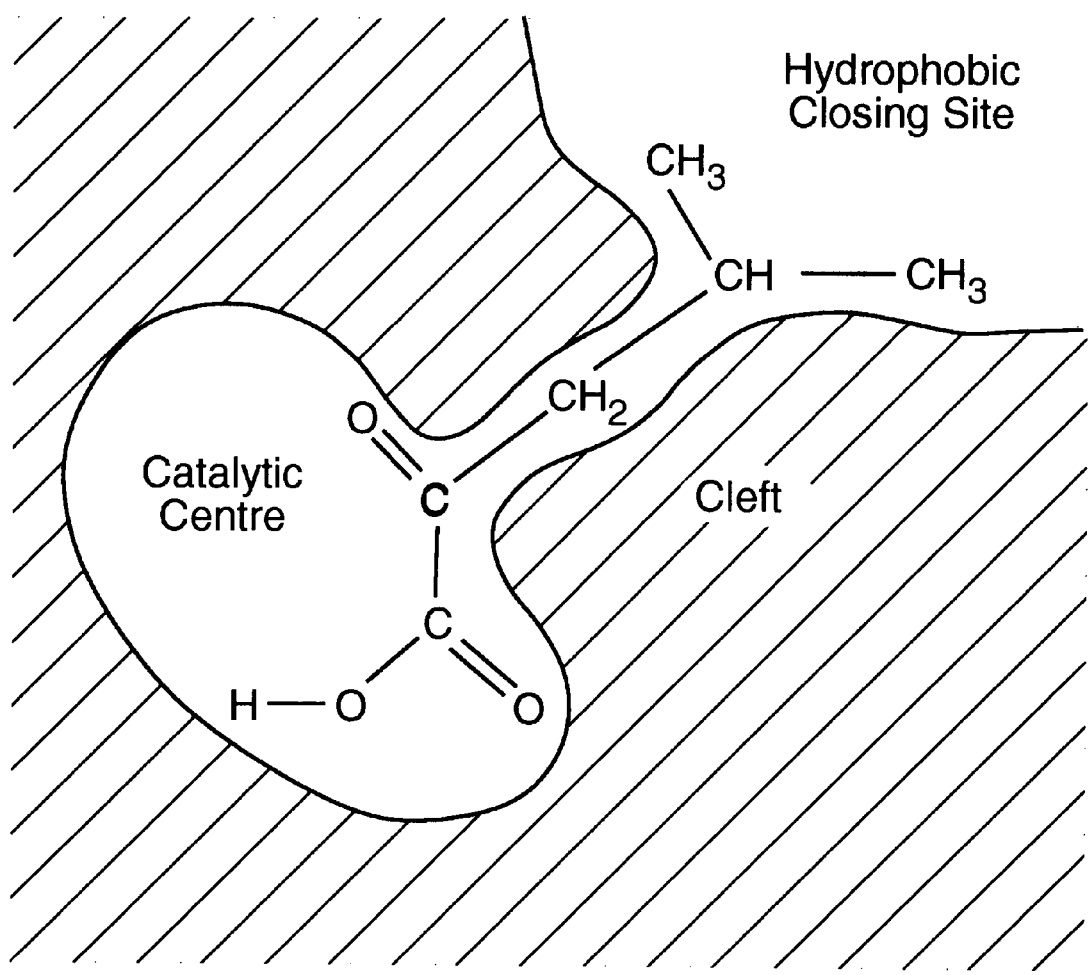
FIG. 1 illustrates what is believed to be the active site of the 2-hydroxy carboxylic acid of the present invention.

The synthesis of chiral 2-hydroxy acids is of considerable importance. These compounds are versatile synthetic intermediaries that may be converted to a variety of compounds with retention of chirality at C-2. These include epoxides, alkyl esters, hydrazinyl esters, $\alpha$-N-alkoxyamino esters and $\alpha$-amino esters. Reactions involving nucleophilic substitution at the 2-position are optimally effected by way of the corresponding 2-triflate esters that are generated in situ and reacted directly with the chosen nucleophile.

The availability of chiral 2-hydroxy acids and esters possessing an additional prochiral functional group in the side-chain offers potential for the synthesis of compounds containing two or more chiral centres. The hydroxyl group at C-2 may be expected to provide an internal control element for this purpose, facilitating stereoselective transformations of the prochiral functional group.

Much effort has been expended in the development of methods to prepare 2-hydroxy acids and esters in chiral form and examples of chemical and enzymatic methods are indicated below. The main limitations of the chemical procedures are technical, since the key transformations all involve the use of water-sensitive reagents at low temperature. Product chirality arises in a stoichiometric sense, either from a chiral auxiliary (substrate control), or from a bulky chiral reductant (reagent control). Asymmetric reduction of 2-keto esters using the chiral borane potassium 9-0-DIPGF-9-BBNH (Brown, H.C., et al, J. Org. Chem., (1986), 51, 3396–3398), requires a stoichiometric quantity of the complex reducing agent and currently only provides access to 2-hydroxy esters of (S)-absolute configuration. Hydroxylation of chiral oxazolidone enolates with oxaziridine oxidants (Evans, D.A., et al, J. Am. Chem Soc., (1985), 107, 4346–4348), requires that, to obtain homochiral 2-hydroxy esters, chromatographic resolution of the 2-hydroxy imide be undertaken before methanolysis. This process gives poor yields in the case of hindered derivatives (e.g. R represents Pr, Bu$^t$). Carboxylation of chiral 2-alkoxy carbanions (Chan, P. C. M., & Chung, J. M., Tet. Lett., (1990), 31, 1985–1988), requires a stoichiometric quantity of the costly reducing agent (R)-BINAP-H and disposal of hazardous tin residues after the transmetauati on stage. Enantioselective reduction of enones catalysed by chiral oxazaborolidines (Corey, E. J., & Bakshi, R. K., Tet. Lett., (1990), 31, 611–614), derives chiralty from a catalytic source in contrast to the above methods. The availability of the optical antipode of the catalyst provides a complementary route to the opposite enantiomeric series. A sequence of four chemical conversions is required to transfom initially-formed chiral alcdhol to the 2-hydroxy ester with obvious cost and yield implications.

The published uses of enzymes found in formation of chiral 2-hydroxy acids include (R)-oxynitfflase- and lipase-based routes. (R)-oxynitrilase-catalysed synthesis of chiral cyanohydrins by hydrolysis (Zeigler, T., et al., Synthesis, (1990), 575–578), gives access to (R)-2-hydroxy acids only. A highly toxic water-free preparation of hydrogen cyanide is required for the enzymatic reaction, which gives variable enantioseleetion to as low as 74%. Resolution of racaemic 2-hydroxy esters catalysed by Pseudomona fluorescens lipase (Kalaritis, P., et al., J. Org. Chem, (1990), 55, 812–815) is one of many examples of enzymatic kinetic isomer resolution. This method is inherently flawed since yields of a particular enantiomer are limited to a maximum of 50%. In practice, the percentage conversion has to be carefully controlled to achieve high optical purities that further reduce the yield.

Since 1950, a number of workers have investigated the reduction of 2-oxo carboxylic acids catalysed by R-hydroxy acid dehydrogenases. For these studies, enzymes isolated from a variety of bacterial sources have been employed. For a given 2-oxo acid, a given enzyme activity may be examined by UV spectroscopy and quantified with the Michaelis constant, Km, and the catalytic turnover, $k_{cat}$.

The basis for the above assay procedure is the strong absorbance at 340 mn of the reduced cofactor NADH compared to the oxidised cofactor $NAD^+$ and the diminution of absorbance with concentration of NADH. The diminution of absorbance, which is direcdy proportional to the concentration of NADH, may be used to estimate the rate of enzymatic reduction of the oxoacid. This technique is limited by several factors including the purity of the enzyme and the assumption that the oxidation of NADH activity correlates to the formation of the expected product.

The key requirement of a biocatalytic reduction is very high enantiomeric purity and high chemical yield. These details are not reported for most of the reactions described in the literature and thus the utility thereof in a chemical reaction remains to be demonstrated. For use in an industrial biocatalytic reduction, further criteria must be safed, such as cost-effectiveness over other methods. This is generally related to the rate of reduction of high concentrations of the substrate by the enzyme and its long-term stability.

Many substrates are identified by optical tests. Only in a few cases have preparative-scale experiments been performed to determine the enantioselectivity of the 2-hydroxy acid produced. For these preparative reactions, a catalytic amount of NADH is employed in conjunction with a regenerating system. This requires a second enzyme, usually formate dehydrogenase (FDH), which uses $NAD^+$ in the oxidation of formate ion to carbon dioxide as previously described (Shaked, Z., & Whitesides, G. M., J. Am. Chem. Soc., (1980), 102, 7104–7105).

To obtain 2-hydroxy acids with (R)-absolute configuration, reduction of 2-oxo acids catalysed by R-lactate dehydrogenases (R-LDH) has also been investigated previously. Recent studies (Simon, E.S., et al., Appl. Biochem. Biotechnol., (1989), 22, 169–179; and Kim, M. J., & Kim J. K., J. Chem. Soc. Chem. Commun., (1991), 326–327), have focussed on R-LDH from *Leuconostoc mesenteroides* (LM-R-LDH) and *Staphylococcus epidermidis* (SE-R-LDH). Only ten compounds have been shown to exhibit measurable activity and of these only the five compounds shown in Table 1 below have been reduced on a preparative scale.

TABLE 1

Preparative scale reductions of 2-oxo- acids using R-lactate dehydrogenase.

| Substrate | Source | Yield % | % ee | Reference |
|---|---|---|---|---|
| H₃C-CH(=O)-CO₂H | LM | 95 | >98 | 1 |
| H₃C-CH(=O)-CO₂H | SE | 86 | >99 | 2 |

TABLE 1-continued

Preparative scale reductions of 2-oxo- acids using R-lactate dehydrogenase.

| Substrate | Source | Yield % | % ee | Reference |
|---|---|---|---|---|
| PhCH₂-C(=O)-CO₂H | LM | 98 | >98 | 1 |
| PhCH₂-C(=O)-CO₂H | SE | 80 | >99 | 2 |
| Ph-CH₂CH₂-C(=O)-CO₂H | SE | 84 | ~100 | 3 |
| cyclopropyl-C(=O)-CO₂H | SE | 86 | >99 | 2 |
| H₃C-CH₂-C(=O)-CO₂H | SE | 92 | >99 | 2 |

LM = *Leuconostoc mesenteroiddis*
SE = *Staphylococcus epidermis*
Ref 1 Simon, E. S., et al, Appl. Biochem. Biotechnol., (1989), 22, 169–179
Ref 2 Kim, M. J., & Kim, J. K., J. Chem. Soc. Chem. Commun., (1991), 326–327
Ref 3 US-A-5,098,841

Turning again to the present invention, the use of optical experiments when combined with preparative scale reductions has been exploited with the present enzyme to predict and confirm the substrate specificity of the enzyme. Results indicate that the enzyme is composed of a catalytic centre separated from a hydrophobic closing site by a cleft which surrounds the 3-carbon and leaves the 4-carbon in the hydrophobic closing site. This enzyme has therefore been demonstrated both practically and by kinetic experiments to exhibit broad substrate specificity which will be suitable for a considerable range of 4- or higher-substituents widely varying in structure and molecular composition. The two compartment model for the binding pocket of the enzyme is illustrated in accompanying FIG. 1. The substrate specificity of the present enzyme as determined by kinetic measurements is indicated in Table 2 below.

TABLE 2

Substrate specificity of *L. Bulgaricus* R-2-hydroxy acid dehydrogenase pH 7.5.

| Substrate HOOC—CO—CH$_2$R | R | Km ($\mu$M)(pH 7.5)$^a$ | $V_m$ (s$^{-1}$)$^b$ | $V_m/K_M$ (s$^{-1}$M$^{-1}$) |
|---|---|---|---|---|
| ketoisocaproate | —CH(CH$_3$)—CH$_3$ | 22 | 20 | 9.1 × 10$^5$ <br> 5 × 10$^6$ (pH 6) |
| ketocaproate | —(CH$_2$)$_2$—CH$_3$ | 20 | 13 | 6.5 × 10$^5$ |
| phenylpyruvate | —C$_6$H$_5$ | 31 | 20 | 6.5 × 10$^5$ |
| benzylpyruvate | —CH$_2$—C$_6$H$_5$ | 36 | 51 | 1.4 × 10$^6$ |
| ketovalerate | —CH$_2$—CH$_3$ | 57 | 19 | 3.3 × 10$^5$ |
| ketobutyrate | —CH$_3$ | 1700 | 47 | 2.8 × 10$^4$ |
| pyruvate | —H | ~20000 | 48 | 2.4 × 10$^3$ |
| ketoisovalerate | CH$_3$—CH——CH$_3$ | ~20000 | 15 | 7.5 × 10$^2$ |
| cyclopentylmethyl | cyclopentyl-CH$_2$ | 10 | 28 | 2.8 × 10$^6$ |

$^a$K$_M$(app): substrate concentration for 0.5 V$_{max}$ at [NADH] = 0.2 mM
$^b$V$_M$(app): turnover at optimal substrate concentration and [NADH] = 0.2 mM The use of 2-oxo carboxylic acid dehydrogenases as catalysts for chiral reductions has to date been restricted to only a limited range of 2-oxo carboxylic acid substrates. Further compounds have been subject to certain spectrophotometric experiments and the inferance is that they are reduced by the enzymatic activity. The success of these reactions is left to interpretation not to analysis. The compounds investigated as substrates have tended to anticipate the boundaries of possibility of useful reduction with 2-oxo carboxylic acid dehydrogenases.

The direct formation of the homochiral 2-hydroxy acid could be performed using 2-oxocarboxylic acid dehydrogenases if substrate specificity was sufficiently broad to overcome the perceived limitation of turnover rate required for a process of anything more than academic curiosity. The present invention now provides an enzyme having the desired range of specificity and exhibiting a significantly improved turnover rate, the sequence variants being even more advantageous.

As indicated above, the present invention provides a means for the production of homochiral 2-hydroxy carboxylic acids or salts thereof, which may, for example, correspond to the following formulae:

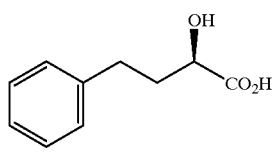

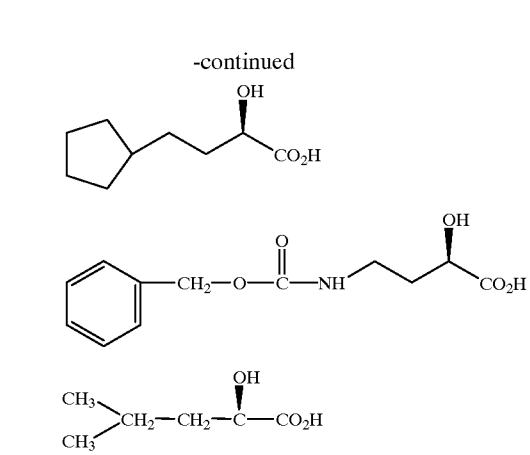

Such compounds have now been prepared with a high yield and an ee >98%.

Results from the preparation of these 2-(R)-hydroxy carboxylic acids or salts, such as sodium or potassium, are given in Table 3 below. An (R)-2-hydroxy acid dehydrogenase obtained from *Lactobacillus delbrueckii* ssp. Bulgaricus is used for the present purposes. Such a reduction is often effected in combination with a recycling NADH reaction.

TABLE 3

Preparative scale reduction 2-keto-carboxylic acid derivatives using 2(R)-hydroxy acid dehydrogenase from *Lactobacillus delbrueckii* ssp. *Bulgarius* (LB2HADH)

| Substrate | Enzyme | Yield % | Purity % ee[a)] |
|---|---|---|---|
| (phenyl-CH₂CH₂-C(O)-CO₂H) | LB2HADH | 92 | >98 ü. |
| (PhCH₂-O-C(O)-NH-CH₂CH₂-C(O)-CO₂H) | LB2HADH | 89 | >99 |
| (isobutyl-CH₂-C(O)-CO₂H) | LB2HADH | 87 | >99 |
| (cyclopentyl-CH₂CH₂-C(O)-CO₂H) | LB2HADH | >99 | >99 |

[a)] after derivitisation of the acid to methyl ester.

As will be appreciated from the foregoing, there have now been identifed 2oxo carboxylic acid substrates for enantioselective reduction using the present 2-hydroxy acid dehydrogenase obtained from *Lactobacillus delbrueckii* ssp. Bulgaricus (LB2HADH). The present enzyme is further defined by the sequence information of Table 4 below.

of the (+)-MPTA Mosher derivative (Dale, J. A., et al, J. Org. Chem., (1969), 34, 2543–2549), by comparison with a racaemic standard. This is the standard literature protocol for chiral analysis of 2-hydroxy acid derivatives and is sensitive enough to detect≦0.5% of the minor diastereoisomer. The Mosher derivatives were prepared by esterification of the

TABLE 4

Gene-derived amino acid SEQ ID NO:1 of the 2-(R)-hydroxy acid
dehydrogenase from *Lactobacillus delbrueckii* ssp. Dulgaricus.

```
1    MTKIAMYNVS PIEVPYIEDW AKKNDVEIKT TDQALTSATV DLAEGCSSVS   (SEQ ID NO:1)
51   LKPLGPVDEE VVYQKLSEYG DKCIGLRIGV FNTINFDWTK KYNLLVTNVP
101  VYSPRAIAEM TVTQAMYLLR KIGEFRYRMD HDHDFTWPSN LISNEINLTV
151  GLIGVGHIGS GLAEIFSAMG AKVIAYDYAY NPEFEPFLTY TDFDTYLKEA
201  DIVSLHTPLF PSTENMIGEK QLKEMKKSAY LINCARGELV DTGALIKALQ
251  DGEIAGAGLD TLAGESSYFG HTARHSEIPE DYKTLAAMPN VVITPHSAFY
301  TETSIRNMVQ ICLTDQLTIA KGRRPRSIVN L
```

Moreover, reductions have been carried out on a preparative scale to permit the isolation and characterisation of 2-hydroxy acids confirming (R)-absolute configuration at the 2-position. The compounds were prepared by reduction using the R-2-hydroxy acid dehydrogenase expressed by a gene from *Lactobacillus delbrueckii* ssp. Bulgaricus and the standard formate/formate dehydrogenase combination to recycle the cofactor NADH in situ. In each reaction the optimum pH was maintained by periodic addition of dilute hydrochloric acid.

The stereo selectivity of the reduction was determined by $^{1}$H- and $^{19}$F-NMR spectroscopy and capillary GC analyses 2-hydroxy acid with ethereal diazomethane, followed by acylation with (+)-MTPA-Cl. For the enzymatic reduction, the substrate was in the form of a salt due to improved solubility and stability over the free acid.

Preparation of a broad substrate specificity 2-(R)-hydroxyy acid dehydrogenase (synonym: 2-(R)-hydroxy acid: $NAD^{+}$-oxidoreductase) from *Lactobacillus delbrueckii* ssg. Bulgaricus.

The gene for this enzyme was isolated from *L. Bulgaricus* (strain LMG 6901=NCIB 11778) by way of a clone pGIN003 (Bernard, N., et al, FEBS Lett., (1991), 290, 61–64). A 1kb fragment between a synthetic BspHI site and an SstI site next to the stop codon was amplified by the polymerase chain reaction and ligated into NcoI-SstI digested pOTSNco12 plasmid. This plasmid is called pGIN113. It was used to transform *E. coli* AR58. The 2-(R)-hydroxy acid dehydrogenase used in this work has an amino acid sequence that corresponds to that given in above Table 4. It may be expected that a (R)-hydroxy acid dehydrogenase which shares greater than 90% identity with that shown in above Table 4 above or the nucleotide sequence data (submitted to GenBank with accession number X65222) may also be capable of performing the reactions of interest.

A typical purification of the enzyme is as follows, (Bernard, N., et al, Eur. J. Biochem., (1994), 224, 439–446): cells (21.1 g wet weight) were harvested from a 2 liter culture of the cell line AR58[pGIN113] grown in Luria broth. The cell culture was induced at 42° C. for 3 hours and then grown overnight at 37° C. before harvesting by centrifugation at 6000 G. The packed cells were resuspended by 50 mM triethanolamine buffer pH 6.5 (IEA). DNAse I (3 mg of Grade II enzyme from Boehringer Mannheim) was added and the suspension was sonicated. Cell debris was centrifuged down for 45 minutes at 30000 G. The supernatant was dialysed against 50 mM sodium citrate buffer, pH 4.5 overnight. A precipitate was removed by centrifugation at 4° C. for 45 minutes at 30000 G. The clear solution was loaded onto a S-Sepharose chromatography column. The active enzyme was not retained, but emerged with the front. The enzyme solution was dialysed against TEA for 18 hours and then applied to a Q-Sepharose column at pH 6.5. The enzyme was eluted by applying a linear gradient of NaCl from 0–0.5 M NaCl in TEA. The purification procedure is summarised in Table 5 below.

TABLE 5

Purification of the 2-(R)-hydroxy acid dehydrogenase from *Lactobacillus delbrueckii* sp. Bulgaricus

| Step | Volume (ml) | Total protein (mg) | Total activity (U) μmol/min | Specific activity (U/mg) | Yield % | Purification - fold |
|---|---|---|---|---|---|---|
| Crude extract | 78 | 507 | 2488 | 4.9 | 100 | 1 |
| S-Sepharose | 104 | 120 | 1924 | 16 | 77.3 | 3.2 |
| Q-Sepharose | 144 | 73 | 1641 | 22.5 | 66.0 | 4.6 |

The substrate specificity of the purified enzyme was established by following the kinetics of reduction of a variety of 2-ketoacids (see Table 2 above). For the wild type enzyme, substrate inhibition was observed in all substrates except for pyruvate and ketoisovalerate, which were not inhibitory. It may be seen that the preferred substrates of *L.Bulgancus* R-hydroxy acid dehydrogenase display a common structural feature consisting of a 3C 2-keto-carboxylic "head" whose 3-carbon is monosubstituted with a hydrophobic "tail", cyclopentylmethylpyruvate being a preferred example. Substrates with more strongly hydrophobic tails (ketocaproate, ketoisocaproate, phenylpyruvate, ketovalerate) are better recognised than ketobutyrate which has only a 1-carbon substituent. The unsubstituted 3C-pyruvate and the 3-carbon branched 5C-ketoisovalerate are both very poorly recognised. This information has been utilised in the preparation of the illustrative FIG. 1, which indicates the nature of the enzyme active site. It is apparent from the preparative scale experiments and the kinetic evaluation that the enzyme is capable of reducing keto acid substrates to R-hydroxy acids of very wide substrate specificity with ʳR groups containing aromatic, amine substituents, the preparative utility of this enzyme may also be limited with substituents by the solubility of the substrate in a solvent compatible to the enzyme reaction.

Having illustrated the isolated and the cloned enzyme, there will now be exemplified a sequence variant.

Glutamine 206 variant of LB2HADH:

A site-directed mutant was prepared from pGIN113 (Bernard, N., et al, Eur. J. Biochem., (1994), 224, 439–446) using a mutagenic oligonucleotide:

5'-ATG GTC TCC CTC C<u>A</u>AACT CCC CTC TTC-3'(SEQ ID NO: 2)

and the Promega "altered sites mutagenesis" kit. The enzyme was purified as for the wild type.

Other examples of site-directed mutants prepared by such a method include R235K, D259N and E264Q.

With 4-cyclopentyl-2-keto-butanoate as substrate, the $k_{cat}$ at 0.2 mM NADH was $25s^{-1}$ (wild type) and $115s^{-1}$ (Q206 mutant), the Km was 8 μM (wild) and 70 μM (Q206) and the Ki was 2 mM substrate (wild) and greater than 100 mM (Q206). The $v_{Q206}/v_{wt}$ was 45 at 70 mM substrate.

Figure 2:
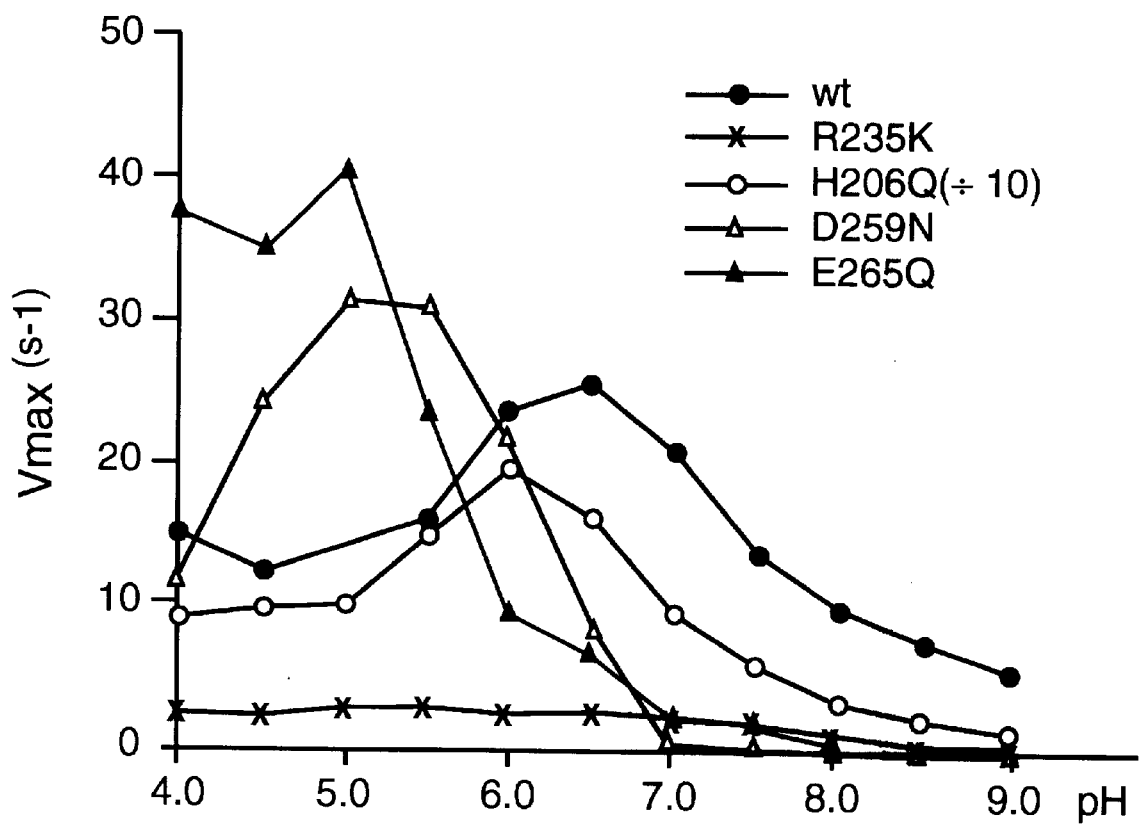
FIG. 2 graphically illustrates a comparison of H206Q and variants of H206, showing that the Vmax for H206Q increased 8-fold.

The advantage of this enzyme of transforming substrate at higher concentrations (20 mM) is shown in accompanying FIG. 2 which compares H206Q and other variants with H206 (wild type) and demonstrates $V_{max}$ increased for H206Q by about 8-fold. This provides the commercial advantages of either using less enzyme or of occupying chemical plant for less time as compared with the wild type.

The use of highly purified enzyme and pure substrates has now proved to be a proficient indicator of relative preparative performance. The results given herein for benzylpyruvate from the kinetic data in Table 2 above and the preparation described where the reaction was complete within 24 hours with 250 units of enzyme contrast with the data in WO 93/13215 where, with 500 units of LDH from *Staphyloccous epidenmidis*, 77 hours was required to complete the reaction. The comparison of preparative reaction time for the formation of 3-cylcopentanyl-2(R)-hydroxypropanoic acid using RLB2HADA to that for LDH from *Staphyloccous epidennidis* was 72 hours v 12 days, with yields of 99% and 60%, respectively. Similarly, in the preparation of the protected amine (R)-N-carbobenzoxy-4-amino-2-hydroxy-butyric acid, equivalent reactions required 1 day and 7 days, respectively, for RLB2HADH and LDH from *Staphyloccus epidermidis*.

Such comparative preparation data illustrate that the present RLB2HADH is improved over the previous disclosures, WO 93/13215 and U.S. Pat. No. 5,098,841, concerning 2-(R)-hydroxyacid dehydrogenic from *Staphyloccus epidennidis*.

These preprative results confirm the kinetic data, which also indicate the broad substrate data, which also indicate the broad substrate compatibility of RLB2HADH.

Further analysis of kinetic properties from specific amino acid changes in the present enzyme and variation in pH as shown in above Tables 2 and 3 demonstrate that key aspects of enzyme mechanism, such as existance of a charge state of active site histidine may change substrate inhibition to a minimum, which will allow simplified reaction conditions to achieve higher product concentrations.

Reduction of Ketoisocaproate Using LB2HADH and Variants

Using purified enzymes, analysis of the pH dependence of the $V_{max}$ was accomplished using 2-ketoisocaproate at 20 mM and coenzyme (0.2 mM). The results are illustrated in accompanying FIG. 2, the $V_{max}$ values for H206Q being divided by 10 to obtain a clearer representation of comparative performance. These data demonstrate the improved catalytic performance of H206Q variant under the conditions, but also show that other sequence variants of LB2HADH are capable of performing the desired reaction with similar performance. (The steady-state kinetic constants of LB2HADH and H206Q in Table 6 below were obtained using standard stopped flow measurements.)

TABLE 6

Steady-state kinetic constants of the wild-type and mutant enzymes

| Enzyme | $K_m$KIC ($\mu$M) | $k_{cat}$ (s$^{-1}$) | $K_i$KIC ($\mu$M) | $K_m$NADH ($\mu$M) | $k_{cat}/K_m$ (s$^{-1}$M$^{-1}$) |
|---|---|---|---|---|---|
| LB2HADH | | | | | |
| pH 5.0 | 25 | 170 | 110 | — | 7.0 × 10$^6$ |
| pH 5.5 | 30 | 240 | 240 | 15 | 8.0 × 10$^6$ |
| pH 6.0 | 50 | 245 | 310 | — | 5.0 × 10$^6$ |
| pH 6.5 | 15 | 75 | 1100 | — | 5.0 × 10$^6$ |
| H206Q | | | | | |
| pH 5.0 | 50 | 570 | 3500 | — | 1.0 × 10$^7$ |
| pH 5.5 | 60 | 310 | 8100 | 110 | 5.0 × 10$^6$ |
| pH 6.0 | 140 | 330 | 5800 | — | 2.5 × 10$^6$ |
| pH 6.5 | 600 | 170 | 7600 | — | 3.0 × 10$^5$ |

The utility of the present invention will now be further exemplified:

Synthesis of (R)-2-hydroxy-4-phenyl butanoic acid

A solution of sodium 2-oxo-4-phenyl butanoate (200 mg, 10 mmol) and sodium formate (0.17 g, 2.5 mmol) in Tris buffer (5 mM; pH adjusted to 7.5 with 2M HCl), NADH (14 mg, 0.02 mM), dithiothreitol (5.0 $\mu$l of a 1M aqueous solution), formate dehydrogenase from yeast (Boehringer Mannheim, 10 mg, 5U) and R-lactate dehydrogenase isolated from *Lacrobacillus delbrueckii* ssp. Bulgaricus (16 mg, 250U see preparation below) were added successively to the solution at room temperature under nitrogen. The mixture was stirred under nitrogen for 24 hours, with periodic addition of HCl (1M; 0.9 ml) to maintain the pH in the range of 6–6.5. The reaction mixture was reduced to half volume in vacuo and, after acidification to pH2, subjected to a normal ethyl acetate (4×70 ml) work-up with brine wash (70 ml) to afford (R)-2-hydroxy-4-phenyl butanoic acid as a white solid (177 mg, 92%). Recrystallisation from tetrachloromethane gave (R)-2-hydroxy-4-phenyl butanoic acid as an amorphous white solid. The title compound gave a melting point of 113–114° C. and an $[\alpha]_D^{22}$ value (c=2.21, EtOH) of −8.4. $^1$H-NMR and capillary GC analysis of the Mosher derivative of the corresponding methyl ester indicated that homochiral (>99.5% ee) product had been obtained.

$\delta$(270MHz, CDCl$_3$) 7.32–7.18 (5H, m, 5-Ph), 4.27(1H, dd, J=8.1, 4H$_2$, 2-H), 2.83–2.79(2H, m, 4-H$_2$), 2.26–1.98 (2H, m, 3-H$_2$); m/z 180(m$^+$, 9%), 162(2), 117 (14), 105 (100), 91 (57).

$^1$H-NMR chemical shifts ($\delta$) of (R)- Mosher derivatives prepared from 2-hydroxy-4-phenyl-butanoate:

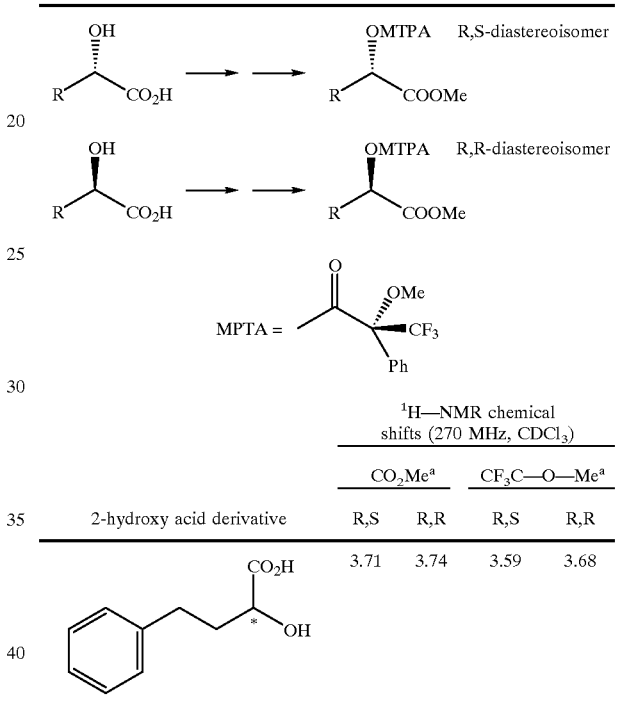

| | $^1$H—NMR chemical shifts (270 MHz, CDCl$_3$) | | | |
|---|---|---|---|---|
| | CO$_2$Me$^a$ | | CF$_3$C—O—Me$^a$ | |
| 2-hydroxy acid derivative | R,S | R,R | R,S | R,R |
| (structure: phenyl-CH$_2$CH$_2$-C*H(OH)-CO$_2$H) | 3.71 | 3.74 | 3.59 | 3.68 |

$^a$Correlation of chemical shifts with absolute configuration at C-2: in all cases the signal for the R,R-diastereoisomer is downfield relative to that for the R,S-diastereoisomer.

Synthesis of 3-cyclopentyl-2-oxopropanoic acid:

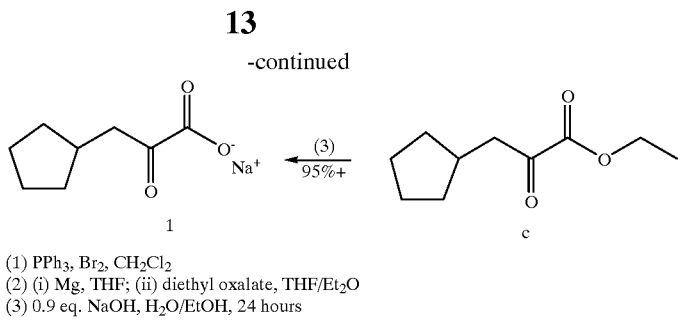

(1) PPh₃, Br₂, CH₂Cl₂
(2) (i) Mg, THF; (ii) diethyl oxalate, THF/Et₂O
(3) 0.9 eq. NaOH, H₂O/EtOH, 24 hours 3-cyclopentanyl-2-oxopropanoic acid 1 was synthesised as illutrated above on 2 g scale. Cyclopentanemethanol a was reacted with bromine and triphenyiphosphine using nitrobenzene as the solvent initially. However, although the product was detected by ¹H-NMR, separation from the nitrobenzene proved ineffective. Use of dichloromethane enabled recovery of the cyclopentanebromomethane b in 82% yield.

Formation of the Grignard from the bromide b and subsequent reaction with diethyl oxalate gave the α-keto ethyl ester c in 84% yield on a 1.5 g scale. Subsequent hydrolysis of c using 0.9 equivalents of ethanolic sodium hydroxide gave the required sodium salt of 1 in 95%+ yield as a white solid.

Preparation of 3-cyclopentanyl-2(R)-hydroxypropanoic acid via RLB2HADH-catalysed reduction:

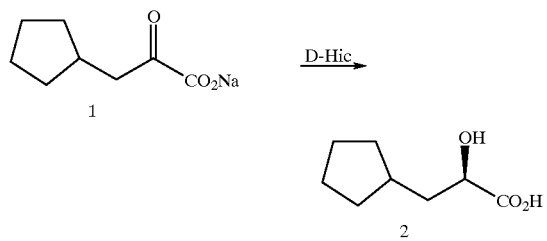

The sodium salt of 3-cyclopentanyl-2-oxopropanoic acid 1 (0.111 g, 0.62 mmol) and sodium formate (0.088 g, 1.3 mmol) in aqueous Tris buffer (25 ml) were deoxygenated by bubbling a strem of nitrogen through the solution for 1.5 hours. Then, dithiothreitol (2 µl) was added, followed by 1 ml of aqueous RLB2HADH solution (5 mg/ml), formate dehydrogenase (13 mg), β-nicotinamide adenine dinucleotide (11 mg). The mixture was stirred under nitrogen for 72 hours. The pH of the solution was maintained between 6 and 7 by addition of dilute aqueous hydrochloric acid (0.1 M). When no further pH change was observed, the solution was acidified to pH 2–3 using sulphuric acid (1M). The mixture was extracted with ethyl acetate (3×25 ml), the combined organic phases were washed with brine (25 ml), dried over anhydrous sodium sulphate and concentrated in vacuo to give 2 as a clear oil (0.129 g, 98.8%). $[\alpha]_D$ −1.50 (c 2, CHCl₃); $\delta_H$ (270 MHz; CDCl₃) 5.90–5.20 (1H, s br, COOH), 4.27 (1H, dd, J 6.04.8, CH(OH)), 2.05 (1H, sep, J 7.0, CH), 1.90–1.70 (4H, m, —CH₂—), 1.68–1.39 (4H, m, —CH₂—), 1.28–1.10 (2H, m, —CH₂—); $\delta_c$ (75 MHz; CDCl₃) 180.0, 70.3, 40.6, 36.5, 33.2, 32.4, 25.4, 25.2; m/z (E.I.) 158 (M⁺, 1.64%), 113 (38), 95 (100) and 83 (46).

A corresponding reaction using LDH from *Staphylococcus epidennidis* achieved a yield of 60% with a reaction time of 12 days.

Preparation of benzyl ³-cyclopentanyl-2(R)-hydroxypropanoate:

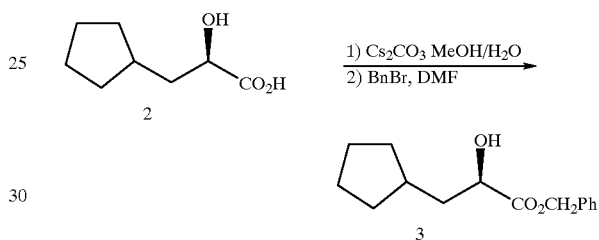

A solution of 3-cyclopentanyl-2(R)-hydroxypropanoic acid 2 (0.049 g, 0.32 mmol) in methanol/water (9:1, 4 ml) was triturated to pH 7 using 20% aqueous caesium carbonate. The solvent was removed in vacuo. Dry DMF (2 ml) was added to the residue and this was again removed in vacuo to give the caesium salt of 2. This salt was suspended in dry DMF (2 ml) and benzyl bromide (0.049 g, 34.2 µl, 0.288 mmol) was added dropwise under nitrogen at 0° C. The mixture was stirred at 0° C. for 2 hours and then at room temperature for a further 20 hours. The solvent was removed in vacuo and the residue partitioned between diethyl ether (15 ml) and water (15 ml). The organic phase was washed with aqueous sodium hydrogen carbonate (3×5 ml) and brine solution (2×5 ml), dried over anhydrous sodium sulphate, filtered and the solvent removed in vacuo. Purification by flash chromatography (silica; 9:1 petroleum ether 40–60: ethyl acetate) yielded 3 as a clear oil (0.048 g, 61%). $[\alpha]_D$ +8.5 (c 4.9, CHCl₃); $\delta_H$ (270 MHz; CDCl₃) 7.40–7.29 (5H, m, Ph), 5.21 (2H, s, CH₂Ph), 4.70 (1H, s, OH), 4.22 (1H, dd, J, 11.8 6.7, CH(OH)), 2.66 (2H, d, J 6, CH₂C=O), 2.00 (1H, sep, J 7.5, CH), 1.82 (2H, m, —CH₂—), 1.78–1.67 (4H, m, —(CH₂)₂—), 1.17–1.03 (2H, m, —CH₂—); $\delta_c$ (75 MHz; CDCl₃) 175.5, 126.9, 127.6, 128.5 128.9, 129.0, 129.1, 70.3, 67.2, 65.3, 36.2, 32.9, 32.2, 25.0, 24.9; m/z (E.I.) 248 (M⁺, 0.87%), 181 (25), 113 (15), 91 (60), 84 (100); (Found: M⁺, 248.142368, C₁₅H₂₀O₃ requires M⁺, 248.141245).

Preparation of the (R)-2-methoxy-2-trifluoromethyl-2-phenylacetyl (MTPA) derivative 4 of benzyl 3-cyclopentanyl-2(R)-hydroxypropanoate obtained from RLB2HADH-catalysed reduction:

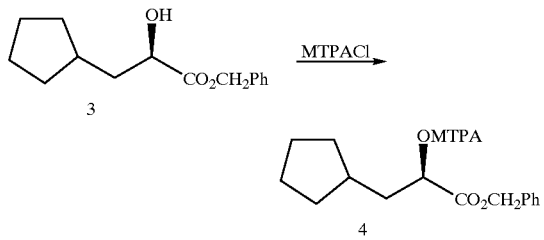

Benzyl 3-cyclopentanyl-2(R)-hydroxypropanoate (0.039 g, 0.155 mmol) was dissolved in dry dichloromethane and pyridine (125 µl), 4,4-dimethyl-aminopyridine (1 mg) and MTPACl (0.078 g, 58 µl, 0.31 mmol) added under nitrogen. The mixture was stirred for 20 hours at room temperature. Diethyl ether (20 ml) was added to the reaction mixture giving a white precipitate. The mixture was washed with water (5 ml), aqueous saturated copper sulphate solution (2×5 ml), saturated sodium hydrogen carbonate solution (5 ml) and brine (5 ml), then dried over anhydrous sodium sulphate and the solvent removed in vacuo giving 4 (0.091 g, 126%) as a clear oil. $\delta_H$ (270 MHz; CDCl$_3$) 7.62–7.11 (10H, m, Ph), 5.21 (2H, s, —C$\underline{H}_2$Ph), 3.61 (3H, s, —OCH$_3$), 2.28–1.98 (1H, m, C$\underline{H}$), 1.94–1.72 (2H, m, —CH$_2$—), 1.60–1.44 (4H, m, —(CH$_2$)$_2$—), 1.44–1.01 (4H, m, —(CH$_2$)$_2$—); m/z (E.I.) 464 (M$^+$, not found), 395 (0.4), 373 (0.6), 357 (0.6), 230 (4), 213 (1), 189 (100), 105 (16) and 91 (86); $\delta_F$ (500 MHz; CDCl$_3$) −71.47 (CF$_3$) e.e. 1612:1 (99.8%). The analysis of ee for material produced using the enzyme LDH from *Staphyloccus epidenridis* was 99.5%.

Preparation of (R)-N-carbobenzoxy-4-amino-2-hydroxy-butyric acid using RLB2HADH:

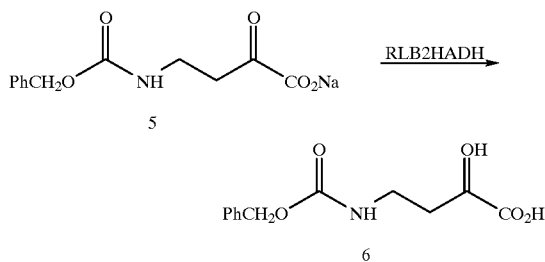

Sodium N-carbobenzoxy4-amino-2-oxobutyric acid 5 (67 mg, 0.25 mmol) and sodium formate (17 mg, 0.25 mmol) in aqueous Tris buffer (20 cm$^3$) were deoxygenated by bubbling a stream of nitrogen through the solution for 30 minutes. RLB2HADH in Tris buffer (0.5 cm$^3$, 2 mg dry mass of enzyme), β-nicotinamide adenine dinucleotide (2 mg), formate dehydrogenase (2 mg) and dithiothreitol (1M, 1 µl) were added and the mixture was stirred at room temperature under nitrogen, the reaction was complete in 1 day. The pH was maintained at from 6.5–7.0 by the addition of dilute aqeuous hydrochloric acid (0.1 M). When no further change in pH was observed, the mixture was concentrated in vacuo. Saturated brine (5 cm$^3$) and concentrated hydrochloric acid (0.5 cm$^3$) were added and the mixture was extracted with ethyl acetate (3×20 cm$^3$). The combined organic phases were dried over anhydrous sodium sulphate and concentrated in vacuo to give (R)-N-carbobenzoxy-4-amino-2-hydroxybutyric acid 6 as an off-white solid (55 mg, 89% yield).

m.p. 70.5° C. (ethyl acetate-petroleum ether), lit. m.p. 76.5–78° C. (ethanol); [α]$_D$ −4.1 (c 10.0, chloroform, 25° C.), lit. [α]$_D$ −5.0 (c 1, chloroform); (Found %: C, 56.8; H, 6.1; N, 5.5. C$_{12}$H$_{15}$O$_5$N requires C, 56.9; H, 5.9; N, 5.5); Found: M$^+$+1, 254.1023. C$_{12}$H$_{16}$O$_5$N requires M+1254.1028); $\delta_H$ 1.88 (1H, m, C$\underline{H}$CHOH), 2.04 (1H, m, C$\underline{H}$CHOH), 3.37 (2H, m, C$\underline{H}_2$NH), 4.26 (1H, m, C$\underline{H}$OH), 5.07 (2H, s, C$\underline{H}_2$Ph), 5.45 (1H, m, NH) and 7.37 (5H, m, Ph); $\delta_c$ 33.6 (C$\underline{H}_2$CHOH), 37.3 (CH$_2$NH), 67.0 (CHOH), 68.2 (CH$_2$Ph), 127.9, 128.0, 128.4, 136.1 (Ph), 157.3 (NC$\underline{O}_2$CH$_2$Ph) and 177.8 (CO$_2$H); m/z (C.I.) 254 (M$^+$+1, 1.5%), 210 (10), 146 (20), 102 (23), 91 (100) and 79 (30).

A corresponding reaction substituting LDH from *Staphylococcus epidemrndis* for RLB2HADH achieved completion at 7 days with a chemical yield of 93%.

The following compounds were also prepared using the above-described procedures:

Preparation of (R)-2-hydroxy-4-methyl pentanoic acid 8 using RLB2HADH:

The sodium salt of 4-methyl-2-oxo-pentanoic acid 7 (152 mg, 1 mmol), RLB2HADH (13.8 mg, 276 U), HCl (1 ml, 1 mmol, 1 eq.). A reaction time of 24 hours gave 8 (114 mg, 0.87 mmol, 87% yield, >99.5% e.e.); $\delta_H^1$ (270 MHz) ppm: 6.63 (1H, br s, 2-OH), 4.29 (1H, br t, J=6.5 Hz, 2-H), 1.95–1.85 (1H, m, 4-H), 1.64–1.60 (2H, m, 3-H$_2$), 0.98–0.95 (6H, 2×s, 5-H$_3$ and 5'-H$_3$).

Preparation of (R)-(2R)-2-O(MTPA)-4-methyl-pentanoic acid methyl ester 10:

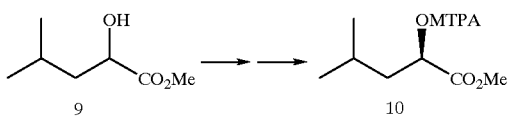

(R)-2-hydroxy-4-methyl pentanoic acid methyl ester 9 (17 mg, 0.117 mmol), (R)-(+)-MTPA (66 µL, 0.351 mmol, 3 eq.), pyridine (21 µl, 1, 0.257 mmol, 2.2 eq.), gave 10 (30 mg, 83% yield); $\delta_H^1$ (400 MHz) ppm: 7.65–7.41 (5H, m, Ph), 5.19 (1H, dd, J=−3.7, 10Hz, 2-H), 3.79 (3H, s, —CO$_2$Me), 3.66 (3H, s, OMe), 1.87–1.80 (1H, m, 4-H), 1.66–1.53 (2H, m, 3-H$_2$), 0.84, 0.83 (6H, 2×d, J=6.4 Hz and J =6.4 Hz, 5-H$_3$ and 5'-H$_3$); $\delta_F^{19}$ (500 MHz) ppm: −71.54 (s, CF$_3$).

It is claimed:

1. A process for the production of a (R)-hydroxy derivative of a 2-keto acid characterized in that it comprises contacting the acid with an enzyme wherein the enzyme is a 2-hydroxy carboxylic acid dehydrogenase derived from *Lactobacillus delbrueckii* ssp. Bulgaricus.

2. The process for the production of a (R) hydroxy derivative of a 2-keto acid acid of claim 1 wherein the enzyme is cloned from *Lactobacillus delbrueckii* ssp. Bulgaricus.

* * * * *

SEQUENCE LISTING

<160> NUMBER OF SEQ ID NOS: 2

<210> SEQ ID NO 1
<211> LENGTH: 331
<212> TYPE: PRT
<213> ORGANISM: L. Bulgaricus

<400> SEQUENCE: 1

```
Met Thr Lys Ile Ala Met Tyr Asn Val Ser Pro Ile Glu Val Pro Tyr
 1               5                  10                  15

Ile Glu Asp Trp Ala Lys Lys Asn Asp Val Glu Ile Lys Thr Thr Asp
                20                  25                  30

Gln Ala Leu Thr Ser Ala Thr Val Asp Leu Ala Glu Gly Cys Ser Ser
            35                  40                  45

Val Ser Leu Lys Pro Leu Gly Pro Val Asp Glu Val Val Tyr Gln
        50                  55                  60

Lys Leu Ser Glu Tyr Gly Asp Lys Cys Ile Gly Leu Arg Ile Gly Val
65                  70                  75                  80

Phe Asn Thr Ile Asn Phe Asp Trp Thr Lys Lys Tyr Asn Leu Leu Val
                85                  90                  95

Thr Asn Val Pro Val Tyr Ser Pro Arg Ala Ile Ala Glu Met Thr Val
            100                 105                 110

Thr Gln Ala Met Tyr Leu Leu Arg Lys Ile Gly Glu Phe Arg Tyr Arg
        115                 120                 125

Met Asp His Asp His Asp Phe Thr Trp Pro Ser Asn Leu Ile Ser Asn
    130                 135                 140

Glu Ile Asn Leu Thr Val Gly Leu Ile Gly Val Gly His Ile Gly Ser
145                 150                 155                 160

Gly Leu Ala Glu Ile Phe Ser Ala Met Gly Ala Lys Val Ile Ala Tyr
                165                 170                 175

Asp Tyr Ala Tyr Asn Pro Glu Phe Glu Pro Phe Leu Thr Tyr Thr Asp
            180                 185                 190

Phe Asp Thr Tyr Leu Lys Glu Ala Asp Ile Val Ser Leu His Thr Pro
        195                 200                 205

Leu Phe Pro Ser Thr Glu Asn Met Ile Gly Glu Lys Gln Leu Lys Glu
    210                 215                 220

Met Lys Lys Ser Ala Tyr Leu Ile Asn Cys Ala Arg Gly Glu Leu Val
225                 230                 235                 240

Asp Thr Gly Ala Leu Ile Lys Ala Leu Gln Asp Gly Glu Ile Ala Gly
                245                 250                 255

Ala Gly Leu Asp Thr Leu Ala Gly Glu Ser Ser Tyr Phe Gly His Thr
            260                 265                 270

Ala Arg His Ser Glu Ile Pro Glu Asp Tyr Lys Thr Leu Ala Lys Met
        275                 280                 285

Pro Asn Val Val Ile Thr Pro His Ser Ala Phe Tyr Thr Glu Thr Ser
    290                 295                 300

Ile Arg Asn Met Val Gln Ile Cys Leu Thr Asp Gln Leu Thr Ile Ala
305                 310                 315                 320

Lys Gly Arg Arg Pro Arg Ser Ile Val Asn Leu
                325                 330
```

<210> SEQ ID NO 2
<211> LENGTH: 27
<212> TYPE: DNA

```
<213> ORGANISM: L. Bulgaricus

<400> SEQUENCE: 2
atggtctccc tccaaactcc cctcttc                                    27
```